United States Patent

Ostrowicki

[11] Patent Number: 5,371,313
[45] Date of Patent: Dec. 6, 1994

[54] PURIFICATION OF HYDROCARBON STREAMS

[75] Inventor: Andreas B. Ostrowicki, Cologne, Germany

[73] Assignee: Polysar Rubber Corporation, Sarnia, Canada

[21] Appl. No.: 158,130

[22] Filed: Nov. 24, 1993

[51] Int. Cl.$^5$ ............................ C07C 1/00; C07C 7/12; C07C 7/00
[52] U.S. Cl. ...................................... 585/642; 585/823; 585/851; 585/852; 585/855; 208/262.1
[58] Field of Search ............... 585/823, 851, 852, 855, 585/642; 208/262.1

[56] References Cited

U.S. PATENT DOCUMENTS 2,920,122  1/1960  Milton et al. .
2,967,819  1/1961  Leum et al. ........................... 208/88
3,864,243  2/1975  Reusser et al. .
4,721,824  1/1988  McWilliams et al. .............. 585/448

OTHER PUBLICATIONS

Chemical Abstracts vol. 30, 2547$^7$, Compt. Rend. 202, 104–6, (1936).
Chemical Abstracts vol. 29, 2874$^3$, Compt. Rend. 200, 612–615 (1935).
Chemical Abstracts vol. 51, 15547e, Brit. 774,125 (May 8, 1957).

*Primary Examiner*—Helen M. S. Sneed
*Assistant Examiner*—Nhat D. Phan
*Attorney, Agent, or Firm*—Joseph C. Gil; Godfried R. Akorli

[57] ABSTRACT

A process is provided for the removal of tertiary butyl chloride from a hydrocarbon stream, wherein the hydrocarbon stream is contacted at a temperature of from about 130° to about 170° C. with a particulate calcium oxide containing from 1 to 10 mole % of a Group 3 or 4 compound and the hydrocarbon stream is recovered containing a reduced level of tertiary butyl chloride.

9 Claims, No Drawings

PURIFICATION OF HYDROCARBON STREAMS

BACKGROUND OF THE INVENTION

The manufacture of butyl rubber involves the polymerization, in methyl chloride, of a mixture of isobutylene and isoprene. The product from the reactor is sent to a flash tank where it is contacted with hot water and steam to vaporize the methyl chloride and unreacted isobutylene and isoprene all of which are recycled by passage through a drier and by distillation. During the process some tertiary butyl chloride is formed which remains with the isoprene from the distillation step. The recycled isoprene contains small amounts of tertiary butyl chloride and cannot be re-used in the polymerization process and is difficult to dispose of because of the presence of the tertiary butyl chloride.

A number of techniques are known for the removal of halogenated organic compounds from hydrocarbons but so far no one procedure is satisfactory, technically and economically, for the removal of tertiary butyl chloride from isoprene so that the isoprene can be re-used in polymerization process. Chemical Abstracts Vol. 30, 2547[7] describes that when n-butyl chloride is heated with calcium oxide, butene is formed. The temperature initially is 275° to 285° C. but after some calcium chloride has been formed the temperature can be reduced to 225° C. Chemical Abstracts Vol. 29, 2874[3] shows that compounds of formula $C_nH_{2n+1}Cl$ yield the hydrocarbon $C_nH_{2n}$ and hydrogen chloride when heated in the presence of catalysts such as aluminum oxide, thorium oxide and calcium chloride. U.S. Pat. No. 2,920,122 describes addition of tertiary butyl chloride to a bed of calcium zeolite A which is then sealed and allowed to stand overnight following which, after removal of the excess tertiary butyl chloride, is heated to recover isobutylene. Chemical Abstracts Vol. 51, 15547 e describes the use of a heating element maintained at 800° to 1100° C. immersed in halogenated hydrocarbons causes removal of hydrogen chloride and shows that for tertiary butyl chloride 87% is converted to isobutylene. U.S. Pat. No. 4,921,924 describes the removal of tertiary butyl chloride from an olefin monomer mixture by contacting the monomer mixture with alumina. U.S. Pat. No. 3,864,243 teaches that hydrocarbons containing organically combined chlorine are treated by passage through high surface area, porous alumina to adsorb the chemically combined chlorine onto the alumina.

SUMMARY OF THE INVENTION

I have discovered that unsaturated mono- and di-olefinic hydrocarbons containing tertiary butyl chloride as an impurity are purified by passage over particulate calcium oxide containing a small proportion of a Group 3 or 4 compound at a temperature of from about 130° to about 170° C.

Accordingly, my invention is a process for the removal of bromine or chlorine from brominated or chlorinated hydrocarbons contained in an unsaturated mono- or di-olefinic hydrocarbon stream by contacting said hydrocarbon stream with particulate calcium oxide containing not less than 1 and not more than 10 mole % (based on the calcium oxide) of a Group 3 or 4 compound maintained at a temperature of from about 130° to about 170° C. and recovering said hydrocarbon stream containing a reduced level of brominated or chlorinated hydrocarbons.

DETAILED DESCRIPTION

The presence of tertiary butyl chloride in hydrocarbon streams can be detrimental to the further use or disposal of such streams. A hydrocarbon stream containing $C_4$-olefins, that is butene-1, butene-2, isobutylene or a mixture thereof, may be contaminated with butyl chlorides in certain industrial processes, for example in the manufacture of polybutenes. A hydrocarbon stream containing pentadiene, that is 1,3-pentadiene, 1,4-pentadiene or a mixture thereof, may be contaminated with chlorinated hydrocarbons in other industrial processes including the separation of pentadiene from other hydrocarbons. A hydrocarbon stream containing isoprene may be contaminated with brominated or chlorinated hydrocarbons including tertiary butyl chloride as in the manufacture of butyl rubber. Thus, the mono- or di-olefinic hydrocarbon stream may contain one or more of such brominated or chlorinated hydrocarbons. The level of brominated or chlorinated hydrocarbons including tertiary butyl chloride in such hydrocarbon streams is usually not more than about 50,000 parts per million by weight based on the total of the hydrocarbon and the brominated or chlorinated hydrocarbon. It is desirable to reduce the brominated or chlorinated hydrocarbon concentration to less than about 1000 parts per million by weight, preferably to less than about 250 parts per million by weight and most preferably to less than about 50 parts per million by weight.

The hydrocarbon stream containing the brominated or chlorinated hydrocarbon is contacted in the liquid or vapor phase with calcium oxide containing the Group 3 or 4 compound in particulate form. The average particle size of the calcium oxide may influence the reaction conditions but generally the calcium oxide has an average particle size not greater than about 5 mm, preferably an average particle size of from about 0.2 to about 5 mm and most preferably from about 0.3 mm to about 2 mm. The Group 3 or 4 compounds are preferably selected from aluminum, cerium, silicon, titanium and zirconium compounds and compounds containing both of aluminum and silica. The calcium oxide containing the Group 3 or 4 compound may be prepared by mixing particulate calcium oxide with the desired Group 3 or 4 compound in particulate form or may be prepared by dry mixing particulate calcium oxide in a slurrying agent such as ethanol with the Group 3 or 4 compound also in a slurrying agent or solvent such as ethanol followed by removal after mixing, as for example by evaporation, of the slurrying agent or agents. The resulting product may be calcined at, for example, about 600° to about 800° C. for a time of about 3 to about 8 hours. Examples of suitable Group 3 or 4 compounds include when dry mixing particulate compounds aluminum oxide, cerium oxide, aluminum silicate, silicon oxide, titanium dioxide and zirconium dioxide and when slurry mixing cerium nitrate, zirconium and titanium alkoxides such as titanium tetra-ethoxide and zirconium tetra-butoxide. When the calcium oxide—Group 3 or 4 compound is calcined, the nature of the Group 3 or 4 compound changes and may form the corresponding oxide or an inter-compound with the calcium, for example calcium titanate. The Group 3 or 4 compound is present in the calcium oxide at not less than 1 and not more than 10, preferably from about 1.5 to about 3, mole % based on the calcium oxide when calculated as the oxide. Preferred Group 3 or 4 compounds contain aluminum, silicon, aluminum-silicon, titanium or zirconium. The particulate calcium oxide may be used as received or may be subjected to a heating stage, for example at 90° to 120° C., for a short period of time. Generally, I have found that I may use the calcium oxide as received. Similarly the calcium oxide containing the Group 3 or 4 compound may be used as mixed or may be subjected to a heating stage, as hereinbefore described, and generally I have found that I may use the material as mixed.

The calcium oxide containing the Group 3 or 4 compound may be used in the form of a static bed over which or through which the hydrocarbon stream may be passed. Alternatively, it may be used in the form of a fluidized bed through which the hydrocarbon stream may be passed. The method of feeding the hydrocarbon stream to the bed is not critical—it may be provided as a liquid or, preferably, as a vapor which preferably is achieved by passing the hydrocarbon stream through a pre-heater so that it contacts the bed as a vapor. Alternatively, it may be provided as a liquid and vaporized on the bed. The pressure in the system may be from atmospheric up to about 5 atmospheres, preferably atmospheric or close to atmospheric.

The temperature at which the brominated or chlorinated hydrocarbon containing stream is contacted with the bed of calcium oxide containing the Group 3 or 4 compound is from about 130° to about 170° C., preferably from about 135° to about 155° C. The stream is contacted with the bed for a time sufficient for the removal of the bromine or chlorine. Generally, the contact may be described in terms of the space velocity (hour$^{-1}$) of the stream over the bed. Suitable space velocities may be within the range of 500 to about 7000 hour$^{-1}$ as a general guide and can readily be established depending on the concentration in the stream of the brominated or chlorinated hydrocarbon, on the temperature and on the particle size of the bed.

The number of beds of the calcium oxide containing the Group 3 or 4 compound is not critical. There may be one bed or there may be two or more such beds.

The concentration of the brominated or chlorinated hydrocarbons in the hydrocarbon stream may be determined by any of the well known analytical methods such as gas chromatography or a combination of gas chromatography and mass spectrometry.

A preferred process is for the removal of chlorine from tertiary butyl chloride in isoprene from a butyl process.

The hydrocarbon stream from the process and containing a reduced level of brominated or chlorinated hydrocarbon may be recovered by well known methods including cooling or compressing and cooling to condense the gas to the liquid state and may be subjected to further purification such as distillation especially if it is desired to remove any other impurities that may be present.

The following Examples illustrate but do not limit the scope of the invention.

EXAMPLE 1

A 94 cm long 1.8 cm diameter steel tube was used as reactor. It was equipped with means to control the rate at which the hydrocarbon stream was fed as a liquid to the reactor, heating and temperature measuring means, a pressure relief valve, and means to remove the treated hydrocarbon stream, in the gaseous form, from the reactor and pass it to a cooling coil immersed either in an ice/salt mixture or dry ice, to collect the treated hydrocarbon. Approximately 150 to 180 g of calcium oxide were placed in the reactor as a bed through which the hydrocarbon stream passed. Analysis of the hydrocarbon stream was by gas chromatography alone or in combination with mass spectrometry. The calcium oxide used (CaO I) was $\frac{1}{4} \times 10$ mesh, an average particle size of about 4.8 mm or (CaO II) was 10 mesh, an average particle size of about 0.6 mm. The hydrocarbon stream was isoprene which contained about 12,600 parts per million by weight of tertiary butyl chloride based on the weight of isoprene and tertiary butyl chloride. The results in Table 1 in which in column 5 tbc means tertiary butyl chloride show that at a temperature of 90° there was little reduction in the tertiary butyl chloride whereas at temperature of 140° and 160° C. there was reduction in the tertiary butyl chloride when $\frac{1}{4} \times 10$ mesh calcium oxide (CaO I) was used and show that at temperatures within the range of 132° to 146° C., there was reduction in the tertiary butyl chloride when 10 mesh calcium oxide (CaO II) was used. This series of experiments is a control series and not part of my invention.

EXAMPLE 2

Using the apparatus described in Example 1, isoprene containing 12,600 parts per million of tertiary butyl chloride was treated using CaO II or calcium oxide (CaO II) containing 2 mole % of a Group 3 or 4 compound. The CaO/Fe$_2$O$_3$ was prepared by powder mixing of calcium oxide and ferric oxide. For the other samples, calcium oxide (200 g) was slurried in 80 to 100 ml of ethanol and thoroughly mixed with a solution in 150 ml of ethanol of one of zirconium butoxide, cerium nitrate, lanthanum nitrate or titanium ethoxide, the ethanol was evaporated and the product was calcined in a furnace at 800° C. for 6 hours to yield calcium oxide containing 2 mole % of the corresponding metal oxide.

The results in Table 2 show that the tertiary butyl chloride is reduced when CaO II is used, that the presence of Fe$_2$O$_3$ does appear to improve the reduction but not significantly, that the presence of cerium oxide or lanthanum oxide does cause a further reduction in the residual tertiary butyl chloride and that the presence of zirconium oxide or titanium oxide causes a significant further reduction to low levels of residual tertiary butyl chloride.

In Table 2, Experiments #1, 2 and 5 are controls outside the scope of my invention. Experiments #3, 4 and 6 are within the scope of my invention and illustrate the reduction of residual tertiary butyl chloride.

TABLE I

| Expt. # | Temp. °C. | Flow Rate ml/min | Space Velocity hour$^{-1}$ | Final tbc ppm | Calcium Oxide Type |
|---|---|---|---|---|---|
| 1 | 60 | 5 | 2610 | 12,000 | I |
| 2 | 90 | 5 | 2850 | 10,600 | I |
| 3 | 140 | 7.5 | 4860 | 4,887 | I |
| 4 | 160 | 6 | 4080 | 1,000 | I |
| 5 | 142–146 | 0.9 | 630 | 1,619 | II |
| 6 | 142–144 | 2.3 | 1580 | 3,916 | II |
| 7 | 142 | 3.9 | 2680 | 4,177 | II |
| 8 | 138–140 | 6 | 4120 | 4,608 | II |
| 9 | 132–144 | 10 | 6860 | 4,113 | II |

TABLE 2

| Expt. # | Temp. °C. | Flow Rate ml/min | Space Velocity hour$^{-1}$ | Final tbc ppm | Calcium Oxide Type |
|---|---|---|---|---|---|
| 1 | 142–144 | 2.3 | 1490 | 3916 | CaO II |
| 2 | 140 | 1.9 | 1300 | 3202 | CaO/Fe$_2$O$_3$ |
| 3 | 140–142 | 2.4 | 1550 | 213 | CaO/ZrO$_2$ |
| 4 | 138–146 | 2.2 | 1425 | 1343 | CaO/CeO$_2$ |
| 5 | 140–144 | 2.1 | 1360 | 2078 | CaO/La$_2$O$_3$ |
| 6 | 138–142 | 2 | 1295 | <5 | CaO/TiO$_2$ |

EXAMPLE 3

The apparatus of Example 1 was used with the addition of a preheater. The preheater was a steel tube, 56 cm long and 1.8 cm diameter and was filled with stainless steel beads of 0.5 cm diameter and was equipped in the same manner as the reactor of Example 1. By this means, the hydrocarbon stream was fed as a liquid to the pre-heater and then passed as a vapor to the reactor. The pre-heater and reactor were both operated at the same temperature. The calcium oxide used was CaO II and the Group 3 or 4 compound was added by dry particle mixing. The hydrocarbon stream was isoprene containing 20,570 parts per million by weight of tertiary butyl chloride based on isoprene plus tertiary butyl chloride.

The results in Table 3 show that compared to the controls (Experiments #1 and 6) reductions in the residual tertiary butyl chloride were achieved.

TABLE 3

| Expt. # | Temp. °C. | Flow Rate ml/min | Space Velocity hour$^{-1}$ | Final tbc ppm | Calcium Oxide Type |
|---|---|---|---|---|---|
| 1 | 142–144 | 0.9 | 585 | 2675 | CaO II |
| 2 | 140–144 | 1.2 | 780 | 713 | CaO/TiO$_2$ |
| 3 | 142–144 | 1 | 650 | 690 | CaO/SiO$_2$ |
| 4 | 144–146 | 1.1 | 715 | <5 | CaO/Al$_2$O$_3$ |
| 5 | 146 | 0.95 | 620 | 52 | CaO/Al$_2$Si$_2$O$_7$ |
| 6 | 140–142 | 0.94 | 610 | 12096 | CaO/0.5% TiO$_2$ |
| 7 | 138–142 | 1.12 | 730 | 9502 | CaO/1% TiO$_2$ |
| 8 | 142–144 | 1.2 | 780 | 713 | CaO/2% TiO$_2$ |
| 9 | 142–144 | 1.05 | 685 | 594 | CaO/4% TiO$_2$ |

What is claimed is:

1. A process for the removal of bromine or chlorine from brominated or chlorinated hydrocarbons contained in an unsaturated mono- or di-olefinic hydrocarbon stream by contacting said hydrocarbon stream with particulate calcium oxide containing not less than 1 and not more than 10 mole %, based on the calcium oxide, of a compound selected from aluminum, cerium, silicon, aluminum-silicon, titanium and zirconium compounds maintained at a temperature of from about 130° to about 170° C. and recovering said hydrocarbon stream containing a reduced level of brominated or chlorinated hydrocarbons.

2. The process of claim 1 wherein said hydrocarbon stream is selected from the group consisting of C$_4$-olefins, isoprene and pentadiene.

3. The process of claim 1 wherein said hydrocarbon stream comprises isoprene.

4. The process of claim 1 wherein said brominated or chlorinated hydrocarbon is tertiary butyl chloride.

5. The process of claim 1 wherein the concentration of brominated or chlorinated hydrocarbon is up to 50,000 parts per million by weight based on the total of the hydrocarbon and brominated or chlorinated hydrocarbon.

6. The process of claim 1 wherein the calcium oxide has an average particle size of from about 0.2 mm to about 5 mm.

7. The process of claim 5 wherein the reduced level of brominated or chlorinated hydrocarbon is less than about 1000 parts per million.

8. The process of claim 3 wherein the temperature is from about 135° to about 155° C., the brominated or chlorinated hydrocarbon is tertiary butyl chloride present at a concentration of up to 50,000 parts per million by weight based on the total of isoprene and tertiary butyl chloride and the reduced level of tertiary butyl chloride is less than about 1000 parts per million.

9. The process of claim 8 wherein the compound is selected from aluminum, silicon, aluminum-silicon, titanium and zirconium compounds.

* * * * *